United States Patent [19]

Kluth et al.

[11] Patent Number: 4,711,959
[45] Date of Patent: Dec. 8, 1987

[54] 2-CYANOAMINO-PYRIMIDINES

[75] Inventors: Joachim Kluth, Langenfeld; Klaus-Helmut Müller, Duesseldorf; Theodor Pfister, Monheim, all of Fed. Rep. of Germany

[73] Assignee: Bayer Aktiengesellschaft, Leverkusen, Fed. Rep. of Germany

[21] Appl. No.: 884,710

[22] Filed: Jul. 11, 1986

[30] Foreign Application Priority Data

Jul. 20, 1985 [DE] Fed. Rep. of Germany ....... 3525977

[51] Int. Cl.$^4$ .................. C07D 239/42; C07D 239/47; C07D 239/46
[52] U.S. Cl. .................. 544/320; 544/321; 544/330; 544/332
[58] Field of Search ................. 544/320, 321, 332, 330

[56] References Cited

U.S. PATENT DOCUMENTS 3,308,119  3/1967  Zimmermann ................. 260/239.75
4,199,583  4/1980  Moon et al. .................... 424/251

FOREIGN PATENT DOCUMENTS 0121082  10/1984  European Pat. Off. .
2501769   7/1976  Fed. Rep. of Germany .

OTHER PUBLICATIONS

McOmie et al., Journal of the Chemical Society (1957) Part II, pp. 1830–1833.
Koppel et al, The Journal of Organic Chemistry (1961) vol. 26, pp. 792–803.
Shigeo Senda and Akio Suzui (1958) vol. 6, pp. 479–482, Chem. Pharm. Bull.
Kaname Takagi and Takeo Ueda (1963) vol. 11, pp. 1382–1388, Chem. Pharm. Bull.

Primary Examiner—John M. Ford
Attorney, Agent, or Firm—Sprung Horn Kramer & Woods

[57] ABSTRACT

A process for the preparation of a 2-cyanoamino-pyrimidine of the formula

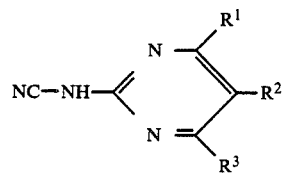

in which
  $R_1$ is hydrogen, halogen, optionally substituted alkyl or optionally substituted alkoxy,
  $R^2$ is hydrogen, alkyl or halogen, and
  $R^3$ is hydrogen, halogen, optionally substituted alkyl or optionally substituted alkoxy, comprising reacting a 2-alkylsulphonyl-pyrimidine of the formula

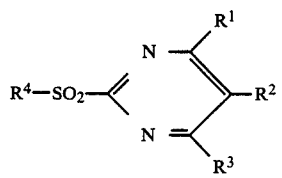

in which
  $R^4$ is optionally substituted alkyl, with cyanamide or with a metal salt of cyanamide at a temperature between 0° and 150° C.

12 Claims, No Drawings

2-CYANOAMINO-PYRIMIDINES

The invention relates to a new process for the preparation of 2-cyanoamino-pyrimidine derivatives, which can be used as intermediates for the preparation of herbicides and plant growth regulators.

It is already known that cyanoamino-heteroarenes are obtained when corresponding halogeno-heteroarenes are reacted with cyanamide salts (compare U.S. application Ser. No. 578,345, filed Feb. 9, 1984; and European Pat. No. A-0,121,082). However, the quality and yield of the products are in many cases unsatisfactory in these reactions.

It is furthermore known that certain cyanoamino-pyrimidines are obtained when β-dicarbonyl compounds are reacted with cyanoguanidine ("dicyandiamide") (compare U.S. application Ser. No. 578,345, filed Feb. 9, 1984). However, 2-cyanoamino-4-hydroxy-pyrimidine derivatives are obtained here, and conversion of these into the 2-cyanoamino-4-alkoxy-pyrimidine derivatives of interest as herbicidal intermediate products is very difficult to carry out and frequently gives an unsatisfactory result.

It has now been found that 2-cyanoamino-pyrimidine derivatives of the general formula (I)

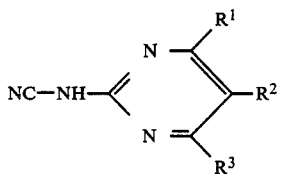
(I)

in which
R¹ represents hydrogen, halogen, optionally substituted alkyl or optionally substituted alkoxy,
R² represents hydrogen, alkyl or halogen and
R³ represents hydrogen, halogen, optionally substituted alkyl or optionally substituted alkoxy, are obtained by a process in which 2-alkylsulphonyl-pyrimidine derivatives of the general formula (II)

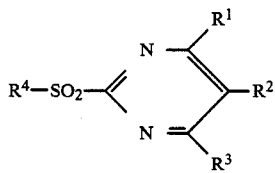
(II)

in which
R¹, R² and R³ have the abovementioned meanings and
R⁴ represents optionally substituted alkyl, are reacted with cyanamide or with metal salts of cyanamide, if appropriate in the presence of a catalyst, if appropriate in the presence of an acid acceptor and if appropriate in the presence of a diluent, at temperatures between 0° and 150° C.

Surprisingly, 2-cyanoamino-pyrimidine derivatives can be prepared in a simple manner in higher yields and a better quality than by known processes by the process according to the invention.

Compounds of the formula (I) which are preferably prepared with the aid of the process according to the invention are those in which
$R^1$ represents hydrogen, fluorine, chlorine, bromine, $C_1$-$C_4$-alkyl [which is optionally substituted by fluorine, chlorine, bromine or $C_1$-$C_2$-alkoxy] or $C_1$-$C_4$-alkoxy [which is optionally substituted by fluorine, chlorine, bromine or $C_1$-$C_2$-alkoxy],
$R^2$ represents hydrogen, methyl, fluorine, chlorine or bromine and
$R^3$ represents hydrogen, fluorine, chlorine, bromine, $C_1$-$C_4$-alkyl or $C_1$-$C_4$-alkoxy [which is optionally substituted by fluorine, chlorine, bromine or $C_1$-$C_2$-alkoxy].

Compounds of the formula (I) which are particularly preferably prepared are those in which
$R^1$ represents hydrogen, methyl, ethyl, chlorine, trifluoromethyl, methoxy, ethoxy or difluoromethoxy,
$R^2$ represents hydrogen or chlorine and
$R^3$ represents hydrogen, chlorine, methyl, ethyl, trifluoromethyl, methoxy, ethoxy or difluoromethoxy.

If, for example, 5-chloro-4-methoxy-6-methyl-2-methylsulphonyl-pyrimidine and sodium cyanamide are used as starting substances, the course of the reaction in the process according to the invention can be represented by the following equation:

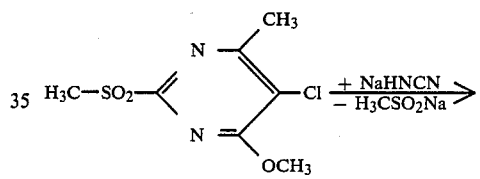

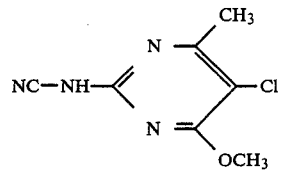

Formula (II) provides a general definition of the 2-alkylsulphonyl-pyrimidine derivatives to be used as starting substances. Preferably, in this formula,
$R^1$ represents hydrogen, fluorine, chlorine, bromine $C_1$-$C_4$-alkyl [which is optionally substituted by fluorine, chlorine, bromine or $C_1$-$C_2$-alkoxy] or $C_1$-$C_4$-alkoxy [which is optionally substituted by fluorine, chlorine, bromine or $C_1$-$C_2$-alkoxy],
$R^2$ represents hydrogen, methyl, fluorine, chlorine or bromine,
$R^3$ represents hydrogen, fluorine, chlorine, bromine, $C_1$-$C_4$-alkyl or $C_1$-$C_4$-alkoxy [which are optionally substituted by fluorine, chlorine, bromine or $C_1$-$C_2$-alkoxy] and
$R^4$ represents $C_1$-$C_4$-alkyl or benzyl.

Particularly preferred starting substances of the formula (II) are those in which
$R^1$ represents hydrogen, methyl, ethyl, chlorine, trifluoromethyl, methoxy, ethoxy or difluoromethoxy,
$R^2$ represents hydrogen or chlorine, R³ represents hydrogen, chlorine, methyl, ethyl, trifluoromethyl, methoxy, ethoxy or difluoromethoxy and R⁴ represents methyl.

Examples which may be mentioned of the compounds of the formula (II) are: 2-methylsulphonyl-pyrimidine, 2-ethylsulphonyl-pyrimidine, 2-benzylsulphonyl-pyrimidine and 4,6-dimethoxy-, 4,6-dimethyl-, 4-methyl-, 4-methoxy-6-methyl-, 4-ethoxy-6-methyl-, 4-chloro-6-methyl-, 4-chloro-6-methoxy-, 4-difluoromethoxy-6-methyl-, 4-methyl-6-methylthio-, 4-chloro-6-ethoxy-, 4-chloro-6-methylthio-, 4-ethyl-, 4,6-diethyl-, 4,6-diethoxy-, 5-chloro-6-methyl-, 5-chloro-4-methoxy-6-methyl-, 5-chloro-4-ethoxy-6-methyl-, 4,5-dichloro-6-methyl-, 4,5-dichloro-6-methoxy-, 4-methoxy-, 4-ethoxy- and 4,6-dichloro-2-methylsulphonyl-pyrimidine, -2-ethylsulphonyl-pyrimidine and -2-benzylsulphonyl-pyrimidine.

The 2-alkylsulphonyl-pyrimidine derivatives of the formula (II) to be used as starting substances are known and/or can be prepared by processes which are known per se (compare J. Chem. Soc. 1957, 1830–1833; DE-OS (German Published Specification) No. 2,501,769; U.S. Pat. specification No. 3,308,119; and J. Org. Chem. 26 (1961), 792).

The compounds of the formula (II) are obtained when 2-alkylthio-pyrimidine derivatives of the formula (III)

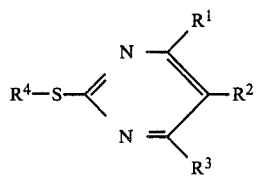

in which

R¹, R², R³ and R⁴ have the abovementioned meanings, are reacted with oxidizing agents, such as, for example, chlorine water or hypochlorous acid or metal salt solutions thereof in water, if appropriate in the presence of organic solvents, such as, for example, methylene chloride, chloroform, carbon tetrachloride or chlorobenzene, at temperatures between −20° C. and +30° C., preferably between −5° C. and +10° C. The working up can be carried out by customary methods. If the products of the formula (II) are obtained as crystals, they can be isolated by filtration with suction. The compounds of the formula (II) can, however, also be taken up in organic solvents, such as, for example, methylene chloride, chloroform or carbon tetrachloride. These compounds are then obtained in a sufficient quality for further reactions after washing the organic solution with water, drying and filtering it and concentrating the filtrate.

The 2-alkylthio-pyrimidine derivatives of the formula (III) required as intermediate products are known and/or can be prepared by processes which are known per se (compare J. Chem. Soc. 1957, 1830–1833; Chem. Pharm. Bull. 5 (1958), 479–482, ibid. 11 (1963), 1382–1388; U.S. Pat. specification No. 4,199,583; U.S. Pat. specification No. 3,308,119; and J. Org. Chem. 26 (1961), 792).

The process according to the invention is preferably carried out in the presence of a diluent. Possible diluents are virtually all the inert organic solvents, but in particular aprotic polar solvents. These include chlorinated hydrocarbons, such as, for example, methylene chloride, chloroform or chlorobenzene, ketones, such as, for example, acetone, methyl ethyl ketone, methyl isopropyl ketone and methyl isobutyl ketone, nitriles, such as, for example, acetonitrile and propionitrile, ethers, such as, for example, diethyl ether, diisopropyl ether, dimethoxyethane, tetrahydrofuran and dioxane, amides, such as, for example, dimethylformamide and dimethylacetamide, and dimethylsulphoxide and sulpholane.

Of the above group of aprotic polar solvents, the following are particularly preferred: dimethylformamide, dimethylacetamide, acetonitrile and propionitrile.

If appropriate, the process according to the invention is carried out in the presence of a catalyst. Preferred possible catalysts here are compounds which are suitable for the phase transfer of anions. Examples which may be mentioned are: benzyltriethylammonium chloride (TEBA), tetrabutylammonium bromide, benzyldimethylhexadecylammonium chloride, benzyldimethyltetradecylammonium chloride, benzyltributylammonium chloride and dodecylethyldimethylammonium bromide.

If appropriate, the process according to the invention is carried out in the presence of an acid acceptor. Compounds which show a comparatively low tendency towards nucleophilic reactions are preferably suitable. These include alkali metal hydrides and alkaline earth metal hydrides, such as, for example, sodium, potassium and calcium hydride, alkali metal carbonates and alkaline earth metal carbonates, such as, for example, sodium carbonate, potassium carbonate and calcium carbonate, and aprotic amines, such as, for example, pyridine, tributylamine, N,N-dimethylbenzylamine and diazabicycloundecene.

Various qualities of cyanamide can be employed for the process according to the invention. The use of metal salts of cyanamide, such as, for example, sodium cyanamide, disodium cyanamide, potassium cyanamide, dipotassium cyanamide and calcium cyanamide, is also possible.

The reaction temperatures can be varied within a substantial range in the process according to the invention. The reaction is in general carried out between 0° C. and 150° C., preferably between 10° C. and 100° C.

The process according to the invention is in general carried out under normal pressure.

For carrying out the process according to the invention, in general between 1 and 2 moles, preferably between 1.1 and 1.5 moles, of cyanamide or the corresponding amount of a metal salt thereof are preferably employed per mole of 2-alkylsulphonyl-pyrimidine derivative of the formula (II). The reaction components are usually brought together at room temperature or with gentle cooling and stirred until the reaction has ended.

For working up, the reaction mixture—if appropriate after being concentrated—is stirred with water and brought to a pH value of between 1 and 7 with an acid, such as, for example, acetic acid, hydrochloric acid or sulphuric acid, and the product of the formula (I) thereby obtained as crystals is isolated by filtration with suction.

The 2-cyanoamino-pyrimidine derivatives of the formula (I) to be prepared by the process according to the invention can be used as intermediate products for the preparation of known herbicides and plant growth regulators (compare DE-OS (German Published Specification) No. 3,334,455; and European Patent A-0,121,082).

PREPARATION EXAMPLES

Example 1

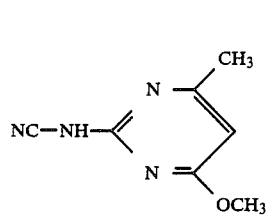

8.0 g (0.06 mole) of potassium carbonate are added to a mixture of 10.1 g (0.05 mole) of 4-methoxy-6-methyl-2-methylsulphonyl-pyrimidine, 2.5 g (0.06 mole) of cyanamide and 100 ml of dimethylformamide at 20° C., while stirring, and the reaction mixture is stirred at 20° C. for 6 hours. It is then concentrated, the residue is stirred with 150 ml of water and the pH value is brought to 6.5 by addition of acetic acid. The product obtained as crystals is isolated by filtration with suction.

6.4 g (78% of theory) of 2-cyanoamino-4-methoxy-6-methyl-pyrimidine of melting point 258° C. (decomposition) are obtained.

The compounds of the formula (I) listed in the following Table 1 can be prepared analogously:

TABLE 1

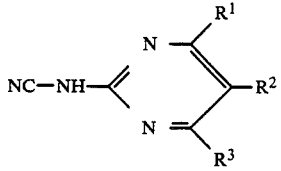

| Example No. | $R^1$ | $R^2$ | $R^3$ | Melting point [°C.] |
| --- | --- | --- | --- | --- |
| 2 | —OCH$_3$ | H | —OCH$_3$ | 202 |
| 3 | H | H | —CH$_3$ | |
| 4 | —CH$_3$ | H | —OCHF$_2$ | 174 |
| 5 | —Cl | H | —OCH$_3$ | 202 (Decomp.) |
| 6 | —Cl | H | —CH$_3$ | |
| 7 | —Cl | H | —OC$_2$H$_5$ | 169 |
| 8 | —CH$_3$ | H | —OC$_2$H$_5$ | 165 |
| 9 | H | H | —C$_2$H$_5$ | |
| 10 | —OC$_2$H$_5$ | H | —OC$_2$H$_5$ | 235 |
| 11 | —Cl | —Cl | —CH$_3$ | |
| 12 | —CH$_3$ | —Cl | —OCH$_3$ | 225 |
| 13 | —CH$_3$ | —Cl | —OC$_2$H$_5$ | 212 |
| 14 | —Cl | —Cl | —OCH$_3$ | |
| 15 | H | H | —OCH$_3$ | amorphous |
| 16 | —Cl | H | —Cl | |
| 17 | —C$_2$H$_5$ | H | —OCH$_3$ | 173 |
| 18 | —OCH$_3$ | —Cl | —OCH$_3$ | 218 |
| 19 | —OC$_2$H$_5$ | —Cl | —OC$_2$H$_5$ | 120 |
| 20 | —CH$_3$ | H | —OC$_3$H$_7$—i | 174 |

PREPARATION OF STARTING SUBSTANCES OF THE FORMULA (II)

Example (II-1)

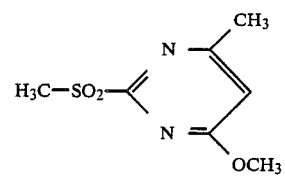

6.8 g (0.04 mole) of 4-methoxy-6-methyl-2-methylthio-pyrimidine are introduced into a two-phase system of 50 ml of water and 100 ml of chloroform and chlorine is passed into this mixture at −5° C. to +5° C., while stirring, until the reaction mixture remains yellow-colored without further addition of chlorine. After subsequently stirring for a short time, while passing through air, the organic phase is separated off, washed with water, dried and filtered and the filtrate is concentrated under a waterpump vacuum.

6.9 g (85% of theory) of 4-methoxy-6-methyl-2-methylsulphonyl-pyrimidine are obtained as a crystalline residue of melting point 80° C.

The compounds of the formula (II) listed in the following Table 2 can be prepared analogously:

TABLE 2

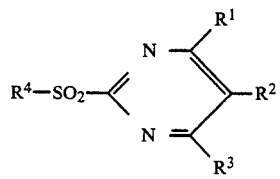

| Example No. | $R^1$ | $R^2$ | $R^3$ | $R^4$ | Melting point [°C.] |
| --- | --- | --- | --- | --- | --- |
| II-2 | —OCH$_3$ | H | —OCH$_3$ | —CH$_3$ | 130 |
| II-3 | H | H | —CH$_3$ | —CH$_3$ | |
| II-4 | H | H | —OCH$_3$ | —CH$_3$ | amorphous |
| II-5 | —CH$_3$ | H | —OCHF$_2$ | —CH$_3$ | |
| II-6 | —Cl | H | —OCH$_3$ | —CH$_3$ | 86 |
| II-7 | —Cl | H | —CH$_3$ | —CH$_3$ | 72 |
| II-8 | —CH$_3$ | H | —OC$_2$H$_5$ | —CH$_3$ | amorphous |
| II-9 | —Cl | H | —OC$_2$H$_5$ | —CH$_3$ | 109 |
| II-10 | —OC$_2$H$_5$ | H | —OC$_2$H$_5$ | —CH$_3$ | |
| II-11 | —Cl | —Cl | —CH$_3$ | —C$_2$H$_5$ | |
| II-12 | —CH$_3$ | —Cl | —OCH$_3$ | —CH$_3$ | 92 |
| II-13 | —CH$_3$ | —Cl | —OC$_2$H$_5$ | —CH$_3$ | 103 |
| II-14 | —Cl | H | —Cl | —CH$_3$ | 123 |
| II-15 | —CH$_3$ | —Cl | —Cl | —CH$_3$ | 97 |
| II-16 | —C$_2$H$_5$ | H | —OCH$_3$ | —CH$_3$ | amorphous |
| II-17 | —OCH$_3$ | —Cl | —OCH$_3$ | —CH$_3$ | 191 |
| II-18 | —OC$_2$H$_5$ | —Cl | —OC$_2$H$_5$ | —CH$_3$ | 110 |

It will be understood that the specification and examples are illustrative but not limitative of the present invention and that other embodiments within the spirit and scope of the invention will suggest themselves to those skilled in the art.

What is claimed:

1. A process for the preparation of a 2-cyanoamino-pyrimidine of the formula

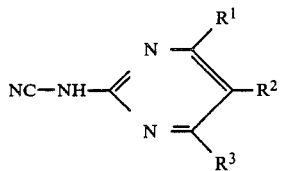

in which
R¹ is hydrogen, halogen, optionally substituted alkyl or optionally substituted alkoxy,
R² is hydrogen, alkyl or halogen, and
R³ is hydrogen, halogen, optionally substituted alkyl or optionally substituted alkoxy, comprising reacting a 2-alkylsulphonyl-pyrimidine of the formula

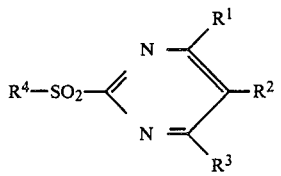

in which
R⁴ is optionally substituted alkyl, with cyanamide or with a metal salt of cyanamide at a temperature between 0° and 150° C.

2. A process according to claim 1, wherein the reaction is carried out at a temperature between 10° and 100° C.

3. A process according to claim 1, wherein the reaction is effected in the presence of a phase transfer catalyst.

4. A process according to claim 1, wherein the reaction is effected in the presence of a phase transfer catalyst selected from the group consisting of benzyltriethylammonium chloride (TEBA), tetrabutylammonium bromide, benzyldimethylhexadecylammonium chloride, benzyldimethyltetradecylammonium chloride, benzyltributylammonium chloride and dodecylethyldimethylammonium bromide.

5. A process according to claim 1, wherein the reaction is effected in the presence of an acid acceptor.

6. A process according to claim 1, wherein the reaction is effected in the presence of an acid acceptor selected from the group consisting of alkali metal and alkaline earth metal hydrides and carbonates, and aprotic amines.

7. A process according to claim 1, wherein the reaction is effected in the presence of a diluent.

8. A process according to claim 1, wherein the reaction is effected in the presence of an aprotic polar solvent as the diluent.

9. A process according to claim 1, wherein the reaction is effected in the presence of an aprotic polar solvent selected from the dimethylformamide, dimethylacetamide, acetonitrile and propionitrile.

10. A process according to claim 1, wherein 1 to 2 moles of cyanamide or the corresponding amount of a cyanamide metal salt are employed per mole of 2-alkylsulphonyl-pyrimidine.

11. A process according to claim 1, wherein 1.1 to 1.5 moles of cyanamide or the corresponding amount of a cyanamide metal salt are employed per mole of 2-alkylsulphonyl-pyrimidine.

12. A process according to claim 9, wherein 1.1 to 1.5 moles of cyanamide or the corresponding amount of a cyanamide metal salt are employed per mole of 2-alkylsulphonyl-pyrimidine and the reaction is effected at a temperature between 10° and 100° C. in the presence of a phase transfer catalyst selected from the group consisting of benzyltriethylammonium chloride (TEBA), tetrabutylammonium bromide, benzyldimethylhexadecylammonium chloride, benzyldimethyltetradecylammonium chloride, benzyltributylammonium chloride and dodecylethyldimethylammonium bromide and in the presence of an acid acceptor selected from the group consisting of alkali metal and alkaline earth metal hydrides and carbonates, and aprotic amines.

* * * * *